United States Patent [19]

Richards

[11] Patent Number: 4,561,293
[45] Date of Patent: Dec. 31, 1985

[54] MATRIC SUCTION SENSOR

[76] Inventor: Lorenzo A. Richards, P.O. Box 3852, Carmel, Calif. 93921

[21] Appl. No.: 535,754

[22] Filed: Sep. 26, 1983

Related U.S. Application Data

[63] Continuation-in-part of Ser. No. 310,295, Oct. 9, 1981, abandoned.

[51] Int. Cl.$^4$ ............................................. G01N 13/00
[52] U.S. Cl. ........................................ 73/73; 73/336.5
[58] Field of Search ................... 73/73, 336.5; 338/34, 338/35, 223; 324/65 P; 429/41, 42

[56] References Cited

U.S. PATENT DOCUMENTS

| | | | |
|---|---|---|---|
| 2,047,638 | 7/1936 | Kott | 73/336.5 |
| 2,589,983 | 3/1952 | Blodgett et al. | 73/336.5 |
| 2,941,174 | 6/1960 | Richards | 73/73 |
| 3,782,179 | 1/1974 | Richards | 73/73 |
| 3,840,407 | 10/1974 | Yao et al. | 429/42 |
| 3,983,527 | 9/1976 | Ohsato et al. | 73/336.5 |

Primary Examiner—Charles Frankfort
Assistant Examiner—Patrick R. Scanlon
Attorney, Agent, or Firm—Limbach, Limbach & Sutton

[57] ABSTRACT

An apparatus measuring the matric suction of soil moisture free from adverse effects due to changes in the salinity and temperature of the soil having first and second water-sensitive resistors and circuit electrically connected to the resistors for measuring the ratio of resistance of the resistors as affected by matric suction. A circuit is provided which includes electrodes proximate opposite sides of each resistor and separate layers located between the water-sensitive resistors and at least all of the electrodes but the electrode furthermost from the soil. The separate layers are chemical inert, electrically conductive, finely divided particles which are wettable by an aqueous solution.

5 Claims, 1 Drawing Figure

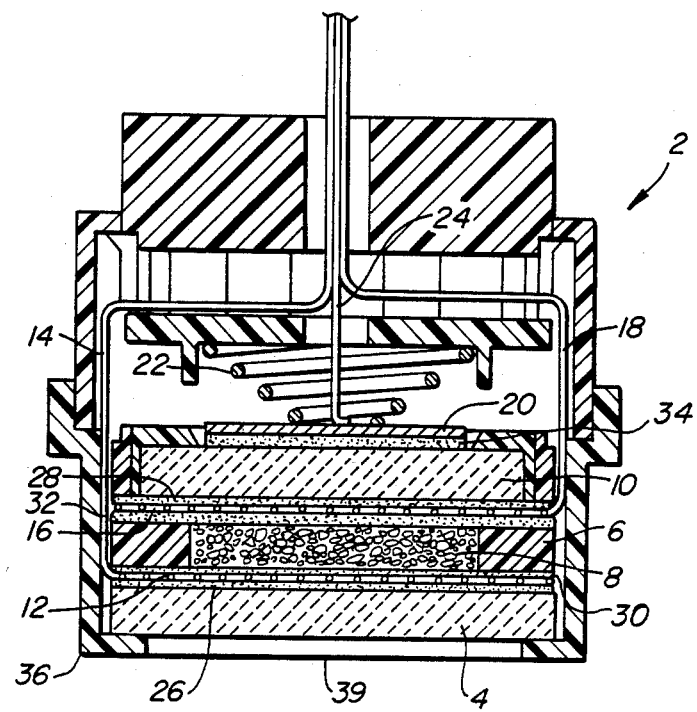

MATRIC SUCTION SENSOR

DESCRIPTION

RELATED APPLICATIONS

The present application is a continuation-in-part of U.S. Application Ser. No. 310,295, filed on Oct. 9, 1981, now abandoned.

TECHNICAL FIELD

A device is disclosed for the measurement of the physical condition of water in soil as it relates to the availability of soil water for plant growth. The ratio of the alternating current resistance of two water-sensitive resistors that are adjacently disposed in soil and which are responsive to matric suction are employed in making measurements free from adverse effect due to changes in the salinity and temperature of the soil.

BACKGROUND ART

In U.S. Pat. No. 3,181,098, a water-sensitive resistor for use in soil is disclosed. The resistor consists of a thin circular layer of suitable, granular, water-absorbant, fill material that is compressed by a sheet of metal into firm contact with a ceramic membrane through a screen electrode. The liquid in the fill is in molecular-diffusional contact with the soil solution through the membrane thus transmitting to the fill the matric suction of the liquid phase of the soil.

The electrolytic resistance of the above-described type of water-sensitive resistor has a stable responsive relation to the matric suction of the soil, at any given temperature and soil salinity condition. As the matric suction of the soil increases, the liquid content of the fill decreases and the electrolytic resistance of the fill between the electrodes increases. However, this resistance also increases if the temperature or salinity of the soil decreases. This negative response is a distinct disadvantage if an uncompensated water-sensitive resistor is used for control in irrigation, either automatically or manually, because plants have less need for water if the soil temperature or salinity decrease. In other words, decreases of soil temperature or salinity actually lessen the need for irrigation, but produce the effect in an electrolytic-resistance type sensor of an increase in matric suction, signalling an increased need for irrigation.

This aberration was substantially completely solved through the invention disclosed and claimed in U.S. Pat. No. 3,782,179. In that disclosure, it is taught that an apparatus for measuring the matric suction of soil could be fabricated which is free from the adverse effects due to changes in the salinity and temperature of the soil by employing two water-sensitive resistors one of which having a relatively coarse pore size distribution causing it to have a relatively large fractional change in resistance for an incremental change in matric suction while the other porous body having a relatively fine pore size distribution causing it to have a relatively small fractional change in resistance for an incremental change in matric suction.

Although the device described and claimed in U.S. Pat. No. 3,782,179 functions adequately for its intended purpose, certain difficulties have been observed particularly regarding the establishment and maintenance of electrical contacts across the water-sensitive resistors. As the reference patent discloses, electric contact across these resistors is most advantageously accomplished by providing grid or screen electrodes in a physically abutting relationship to parallel flat surfaces of the resistors. The screens or grids can be formed by a sputtered metal film which is, in turn, electrically connected to wires emanating from the device.

Unfortunately, unless gold or an equivalent noble metal is employed for fabricating electrodes from thin films, the electrolytic effect to which the electrodes are subjected causes a rapid and accelerated corrosive deterioration which greatly reduces the operating life of the device. In that gold and equivalent metals are prohibitively expensive, a serious drawback remained in practicing the invention as described and claimed in U.S. Pat. No. 3,782,179.

It is thus an object of the present invention to describe an apparatus for measuring the matric suction of soil which is free of the disadvantages outlined above inherent in the prior art.

It is yet another object of the present invention to describe an apparatus for measuring the matric suction of soil which possesses a usable functional life greatly extended as compared to similar apparatus taught by the prior art.

These and further objects of the present invention will be more readily appreciated when considering the following disclosure and the appended drawing which is a cross-sectional view of the apparatus of the present invention.

SUMMARY OF THE INVENTION

An apparatus measuring the matric suction of soil free from adverse effects due to changes in the salinity and temperature of the soil having first and second water-sensitive resistors and circuit means electrically connected to the resistors for measuring the ratio of resistance of the resistors as affected by the matric suction of adjacent soil. Circuit means is provided which includes electrodes proximate opposite sides of each resistor and separate layers located between the water-sensitive resistors and at least all of the electrodes but the electrode furthermost from the soil, said separate layers comprising substantially chemical inert, electrically conductive, finely divided particles which are wettable by an aqueous solution.

BEST MODE FOR CARRYING OUT THE INVENTION

Referring to the appended FIGURE, reference numeral 2 designates, generally, the sensing device incorporating the present invention. As is shown therein, the device is provided with an electrically non-conductive porous ceramic plate 4 that can be placed in contact with and buried in soil. Soil moisture passes through case opening 39 and ceramic plate 4 into the chamber defined by external walls 36. A plastic ring 6 is shown as enclosing a space filled with an electrically non-conductive granular material 8 which can be, for example, silica or quartz having a relatively coarse pore size distribution as compared to the second resistor 10. Resistor 10 comprises a disc of electrically non-conductive ceramic material which is of a fine porosity and which will absorb moisture passing through electrically non-conductive granular material 8.

A screen electrode 12, comprised of, for example, stainless steel, is positioned between ceramic material 4 and resistor 8 and is provided with lead 14 which communicates to the exterior of the device. Between resistors 8 and 10 is a second screen electrode 16 provided with lead 18 as shown. Plate electrode 20 is preferably spring-pressed, by spring 22, against resistor 10 and also provided with lead 24 whereby the three electrodes may be connected to a suitable bridge circuit for measuring the matric suction, all as described in U.S. Pat. No. 3,782,179.

Moisture from the adjacent soil passes through opening 39 in the plastic case and through ceramic disc 4 into resistors 8 and 10. As the matric suction increases, moisture is withdrawn from the apparatus and the relatively large spaces between the granules of resistor 8 become filled with air which changes the resistance characteristics of the resistor. By comparing the resistance of the resistors 8 and 10 in a Wheatstone bridge circuit, one can accurately determine the matric suction free from adverse effects due to changes in salinity and temperature of the adjacent soil.

As stated previously, however, the electrolytic effects due to the presence of an electric current and ambient moisture surprisingly accelerates the corrosive action upon the screen electrodes 12 and 16 to such a degree that the life expectancy of the device is unacceptably short. As a means of solving this problem, separate layers of graphite 26, 28, 30 and 32 are provided which are located between the water-sensitive resistors and at least all of the electrodes but the electrode furthermost from the soil (element 20) which comprise substantially chemically inert, electrically conductive, finely divided particles which are wettable by an aqueous solution. Although such a separate layer can also exist, as shown in the FIGURE as element 34 between ceramic layer 10 and electrode 20, it is only mandatory in practicing the present invention that the separate layers, as decribed above, be provided as shown as elements 26, 28, 30 and 32 to enable water from the ambient soil to penetrate both resistive layers 8 and 10. The material, preferably finely divided graphite, can be caused to substantially fill the spaces between the above-recited resistors to provide a good electrical connection between the electrodes and resistors, that is, between the electrodes and the moisture contained in the resistors.

In practice, the electrodes can be formed separately and subsequently embedded within the conductive separate layers which can be caused to completely encase the electrodes and complete an excellent electrical contact. If graphite is employed as the separate layer, it has been found that conventional lubricating grade graphite available from Union Carbide Company performs well in practicing the present invention.

While a particular arrangement of resistors has been shown and described herein, the same is merely illustrative of the principals of the invention and other arrangements may be resorted to within the scope of the appended claims.

I claim:

1. An apparatus for measuring the matric suction of soil free from adverse effects due to changes in the salinity and temperature of the soil comprising:

a case having an opening therein for the passage of moisture to and from the soil and interior of the case;

first and second water-sensitive resistors characterized as being porous, compact bodies wettable by water found in the surrounding soil, said first water-sensitive resistor located relatively closer to said openings as compared to said second resistor and having a relatively coarse pore size distribution as compared to the second resistor;

circuit means electrically connected to said resistors for measuring the ratio of resistance of said resistors as affected by matrix suction, said circuit means including electrodes proximate opposite sides of each resistor; and separate layers located between said water-sensitive resistors and at least all of said electrodes but the electrode located on said second resistor on its surface located furthest from said opening, said separate layers comprising substantially chemically inert, electrically conductive finely divided particles, which are wettable by an aqueous solution.

2. The apparatus of claim 1 wherein said separate layers are comprised of powdered graphite.

3. The apparatus of claim 1 wherein said first and second resistors are superimposed discs having one electrode between said discs and one of said separate layers contacting both said discs and electrode.

4. The apparatus of claim 1 wherein at least all of the electrodes but the electrode furthermost from the opening are of a screen configuration.

5. The apparatus of claim 4 wherein said electrodes having a screen configuration are embedded in said separate layers.

* * * * *